United States Patent
Woodruff et al.

(10) Patent No.: US 8,550,981 B2
(45) Date of Patent: Oct. 8, 2013

(54) IMPLANTABLE PORT WITH VIBRATORY FEEDBACK

(75) Inventors: Scott A. Woodruff, Cincinnati, OH (US); Amy L. Marcotte, Mason, OH (US); Timothy G. Dietz, Terrace Park, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 825 days.

(21) Appl. No.: 12/640,048

(22) Filed: Dec. 17, 2009

(65) Prior Publication Data

US 2011/0152901 A1 Jun. 23, 2011

(51) Int. Cl.
*A61F 2/00* (2006.01)

(52) U.S. Cl.
USPC .......................................................... 600/37

(58) Field of Classification Search
USPC ............ 600/37; 606/151, 157, 192; 604/272
See application file for complete search history.

(56) References Cited

U.S. PATENT DOCUMENTS

| | | | |
|---|---|---|---|
| 4,760,837 A | 8/1988 | Petit | |
| 5,107,155 A | 4/1992 | Yamaguchi | |
| 5,277,694 A | 1/1994 | Leysieffer et al. | |
| 5,800,336 A | 9/1998 | Ball et al. | |
| 6,461,292 B1 | 10/2002 | Forsell | |
| 6,470,892 B1 | 10/2002 | Forsell | |
| 6,982,696 B1 | 1/2006 | Shahoian | |
| 7,292,227 B2 | 11/2007 | Fukumoto et al. | |
| 7,351,240 B2 | 4/2008 | Hassler, Jr. et al. | |
| 7,390,294 B2 | 6/2008 | Hassler, Jr. | |
| 7,416,528 B2 | 8/2008 | Crawford et al. | |
| 7,442,165 B2 | 10/2008 | Forsell | |
| 7,583,564 B2 | 9/2009 | Kitahara et al. | |
| 7,599,744 B2 | 10/2009 | Giordano et al. | |
| 7,621,863 B2 | 11/2009 | Forsell | |
| 2005/0283118 A1 | 12/2005 | Uth et al. | |
| 2006/0190039 A1* | 8/2006 | Birk et al. | 606/219 |
| 2006/0211914 A1 | 9/2006 | Hassler, Jr. et al. | |
| 2007/0149947 A1 | 6/2007 | Byrum | |
| 2008/0250340 A1 | 10/2008 | Dlugos, Jr. et al. | |
| 2009/0306462 A1* | 12/2009 | Lechner | 600/37 |

FOREIGN PATENT DOCUMENTS

WO WO 01/23023 4/2001

OTHER PUBLICATIONS

Dietz, T. et al., "Partially Implantable Vibrating Ossicular Prosthesis," Transducers '07, vol. 1 (Jun. 16-19, 1997) pp. 433-436.
International Search Report dated Mar. 18, 2011 for Application No. PCT/US2010/059137.

* cited by examiner

*Primary Examiner* — Christine Matthews
(74) *Attorney, Agent, or Firm* — Frost Brown Todd LLC

(57) ABSTRACT

A system includes an adjustable gastric band coupled with an injection port. The port includes sensors, a plate beneath a septum, and a vibration generator in communication with the sensors. A first sensor detects palpation through a patient's skin when the injection port is implanted in the patient. The vibration generator provides a vibratory response to detected palpation, thereby providing haptic feedback to a physician who is attempting to locate the injection port by palpating the patient. A second sensor detects a needle striking the plate, and the vibration generator provides a vibratory response to a detected needle strike. The vibration generator thereby provides haptic feedback to a physician to confirm that the needle has been successfully inserted through the septum. A pressure sensor may be used to provide vibratory feedback to the patient to indicate that an adjustment to the band is needed.

13 Claims, 6 Drawing Sheets

IMPLANTABLE PORT WITH VIBRATORY FEEDBACK

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Fluid may be added to the bladder by using a syringe and needle (e.g., Huber needle) to inject the fluid through an implanted injection port that is coupled with the bladder. Similarly, fluid may be removed from the bladder by using a syringe and needle to withdraw the fluid through the implanted injection port.

In some settings, it may be desirable to facilitate location of an injection port, such as to assist in targeting with a needle. Various examples of devices and methods for locating an injection port via RF telemetry are disclosed in U.S. Pub. No. 2006/0211914, entitled "System and Method for Determining Implanted Device Positioning and Obtaining Pressure Data," published Sep. 21, 2006, the disclosure of which is incorporated by reference herein.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
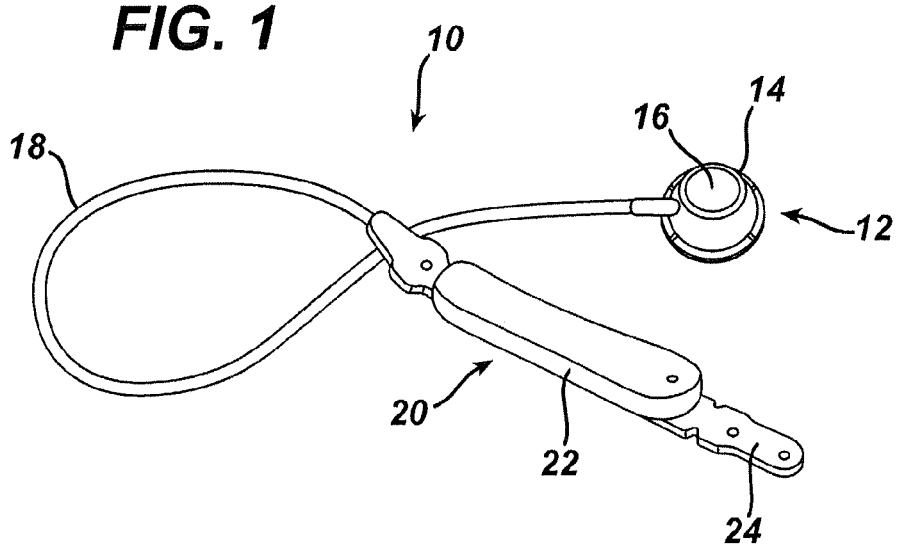
FIG. 1 depicts a perspective view of an implantable portion of an exemplary gastric band system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIGS. 1-4 illustrate an exemplary gastric band system (10). As shown, gastric band system (10) comprises an injection port (12), a gastric band (20), and a catheter (18), which together form a closed fluid circuit. Injection port (12) of the present example comprises a housing (14) and a needle penetrable septum (16). Housing (14) defines a fluid reservoir (not shown), such that a needle may pierce septum (16) to reach the reservoir and add or withdraw fluid (e.g., saline, etc.) as described in greater detail below. Housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. Injection port (12) may be secured at approximately 10 cm below the surface of the patient's skin or at any other suitable depth. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, the disclosure of which is incorporated by reference herein. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20). In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
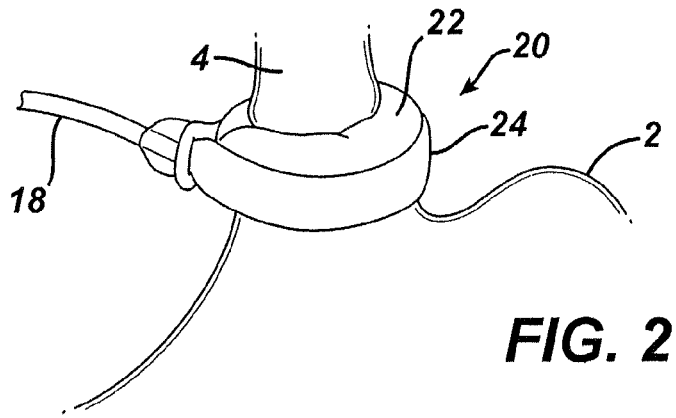
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastroesophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
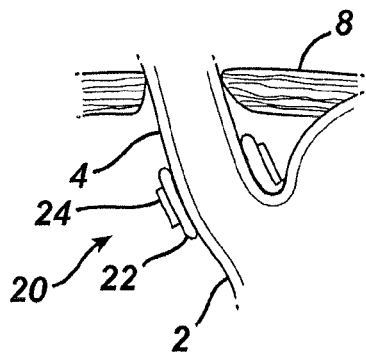
FIG. 3 depicts a cross-sectional view of the gastric band of FIG. 1, showing the band positioned around the gastro-esophageal junction of a patient in a deflated configuration.
Figure 4:
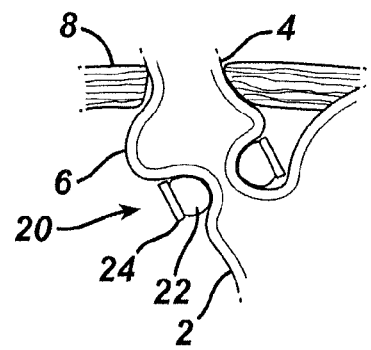
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient. After gastric band system (10) has been implanted in the patient and an initial amount of fluid (e.g., saline, etc.) has been introduced to gastric band system (10), a physician may need to occasionally adjust the amount of fluid in gastric band system (10) by using a needle (e.g., Huber needle, etc.) that is inserted through septum (16) of injection port (12). For instance, such adjustments may be desirable to account for weight loss achieved by the patient, and may be started around one month (or any other suitable time period) after gastric band system (10) has been implanted.

Figure 5:
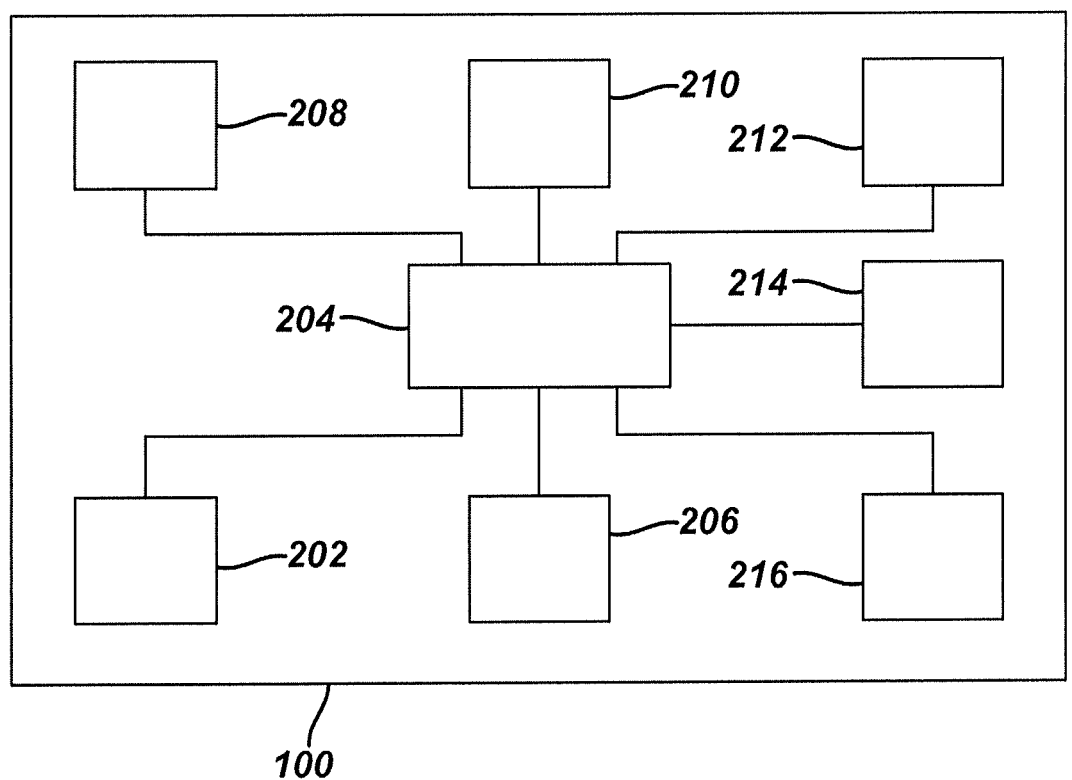
FIG. 5 depicts a block diagram of components of an exemplary injection port usable with the gastric band system of FIG. 1.

FIGS. 5-8 illustrate an exemplary injection port (100) that may be used in gastric band system (10), as a substitute for the relatively simpler injection port (12) shown in FIG. 1. FIG. 5 shows various electrical and electromechanical components of injection port (100) in block diagram form. These electrical and electromechanical components will be described in greater detail below. However, several mechanical components and features of injection port (100) will be discussed first, with reference to FIGS. 6-8.

Figure 6:
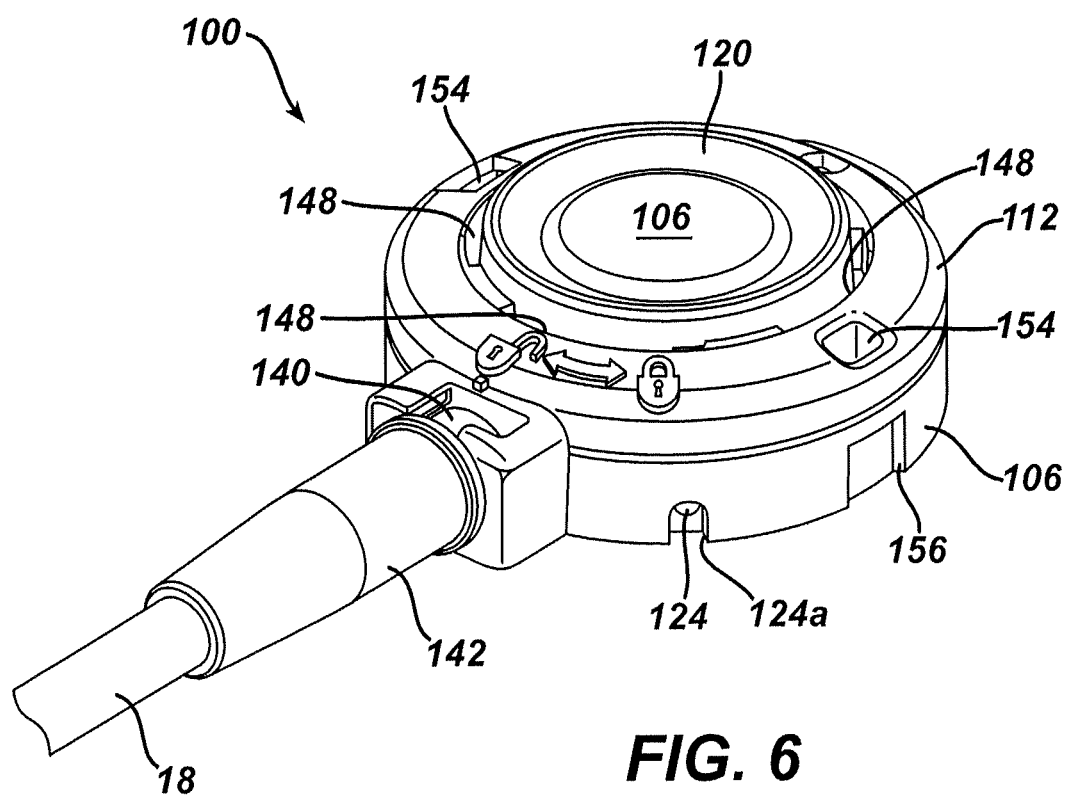
FIG. 6 depicts a perspective view of the injection port of FIG. 5.
Figure 7:
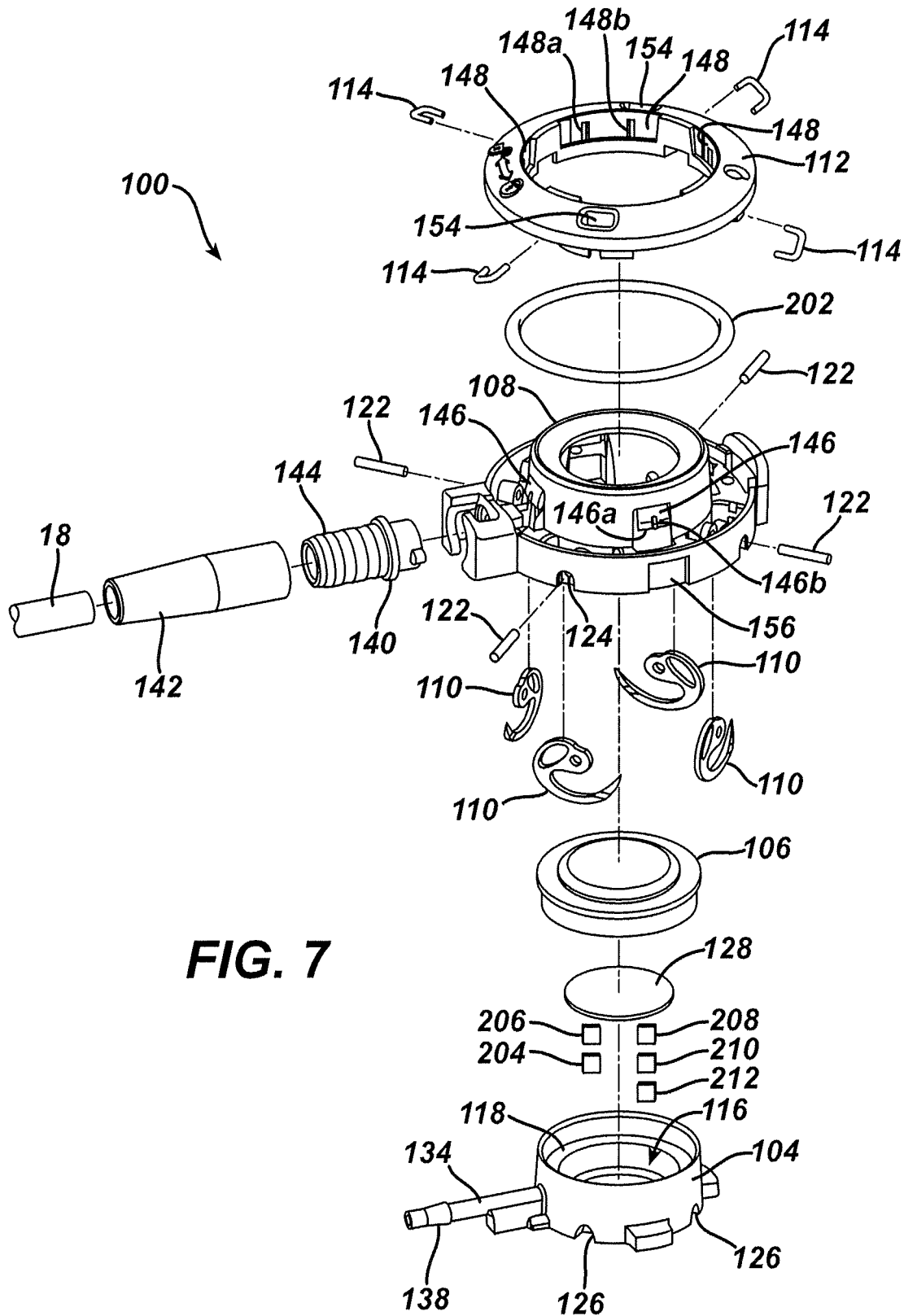
FIG. 7 depicts an exploded view of the injection port of FIG. 5.
Figure 8:
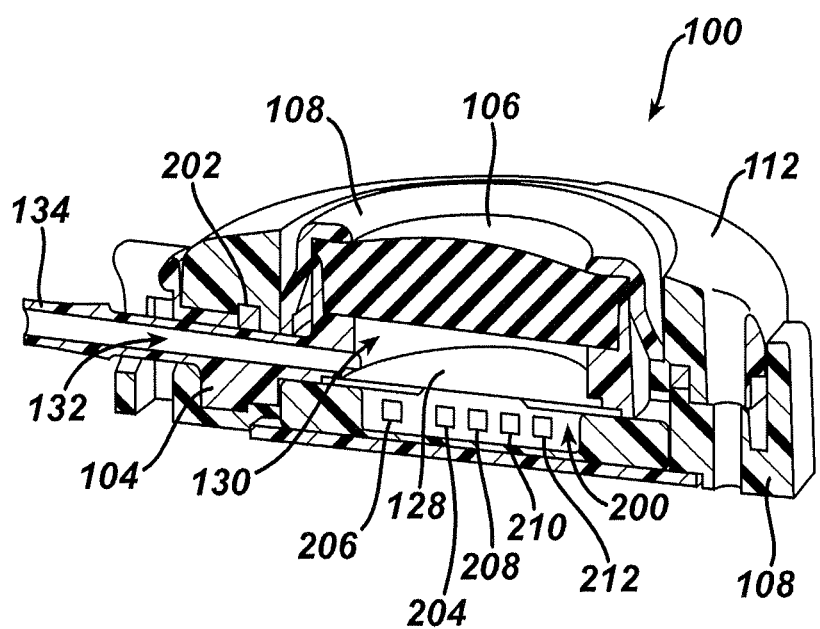
FIG. 8 depicts a cross-sectional view of the injection port of FIG. 5.

In the present example, and as shown in FIGS. 6-8, injection port (100) comprises septum retainer (104), septum (106), and port body (108). Injection port (100) also includes an integrally constructed attachment mechanism, which comprises rotating fasteners (110), actuator (112), and a plurality of link members (114). Septum (106) is disposed partially within internal cavity (116) of septum retainer (104), adjacent annular flat (118). Septum (106) may be formed of any suitable material or combination of materials, including but not limited to biocompatible silicone. Septum retainer (104), port body (108), and actuator (112) may be made of any suitable biocompatible material or combination of materials, including but not limited to polyetheretherketon (PEEK). Fasteners (110) and link members (114) may be made of any suitable biocompatible material or combination of materials, including but not limited to stainless steel. Port body (108) includes annular rim (120), which engages the upper surface of septum (106) to compress and retain septum (106) against septum retainer (104). Annular rim (120) slopes inwardly toward septum (106) in the present example. Annular rim (120) is thus configured to assist in guiding a needle toward septum (106) when a needle engages annular rim (120). Port body (108) is retained to septum retainer (104) by a plurality of pins (122) which are disposed through respective holes (124) in recesses (124a) formed in port body (108) and which extend inwardly into respective recesses (126) formed about the bottom periphery of septum retainer (104). Pins (122) may be made of any suitable biocompatible material or combination of materials, including but not limited to stainless steel.

Plate (128) is disposed in recess (116a) formed in the bottom of septum retainer (104), underlying septum (106). Plate (128), septum retainer (104), and septum (106) together form a fluid chamber or reservoir (130). In the present example, plate (128) is formed of metal (e.g., stainless steel), though it should be understood that any other suitable material or combination of materials may be used. When a needle is inserted through septum (106) to introduce or withdraw fluid from fluid chamber (130), such as in order to adjust the size of adjustable gastric band (20), metallic plate (128) will protect septum retainer (104) from puncture and provide tactile feedback to the surgeon through the needle to indicate that the needle has bottomed in reservoir (130). Additional tactile feedback may be provided by a vibration generator (210), as will be described in greater detail below. Plate (128) may be secured to septum retainer (104) in any suitable manner (e.g., retaining lip, etc.). By way of example only, plate (128) may be insert molded in septum retainer (104).

Septum retainer (104) also includes passageway (132), which is in fluid communication with fluid chamber (130). Passageway (132) is defined by fitting (134) extending from the periphery adjacent the bottom of retainer (104). Catheter (18), which may lead to and be in fluid communication with adjustable gastric band (12), is connected to fitting (134), being compressingly urged against annular rib (138) by connector (140). Connector (140) is disposed about catheter (18) and is secured to port body (108). Sleeve (142) is disposed about catheter (18) and is secured to connector (140) by annular ribs (144). Sleeve (142) relieves strain on catheter (18), preventing catheter (18) from kinking when loaded laterally. Of course, catheter (18) may alternatively couple with injection port (100) in any other suitable way.

Actuator (112) of the present example is secured to port body (108). Although in the embodiment depicted actuator (112) is illustrated as an annular ring rotatably supported by port body (108), actuator (112) may have any other suitable configuration and be supported in any suitable manner Actuator (112) of the present example is rotatable relative to port body (108) to move fasteners (110) between and including deployed/extended and undeployed/retracted positions. As seen in FIG. 7, port body (108) includes a plurality of downwardly and outwardly extending tabs (146). There are four equally spaced tabs (146) in the present example, though any other suitable number of tabs (146) may be used in any other suitable arrangement. Actuator (112) includes an equal number of corresponding recesses (148). To assemble actuator (112) to port body (108), recesses (148) are aligned with tabs (146), and pushed down, temporarily deflecting tabs (146) inwardly until tabs (146) reach recesses (148) and move outwardly to dispose lower edges (146a) in recesses (148) such that actuator (112) is retained thereby. The lengths of tabs (146) and depth of recesses (148) allow some axial end play between actuator (112) and port body (108), as will be described below. Actuator (112) may rotate generally about the central axis of port body (108). In the present example, actuator (112) may rotate through an angle of about 40 degrees, although any suitable angle may be used.

In the present example, when actuator (112) is at a first rotational position relative to port body (108), fasteners (110) are in an undeployed or retracted position. When actuator (112) is rotated to a second rotational position relative to port body (108), fasteners (110) are moved to a deployed or extended position. Actuator (112) may be moved back and forth between the first and second rotational positions to selectively deploy/extend or undeploy/retract fasteners (110). A detent system is formed by a pair of spaced apart raised detent ribs (148a, 148b) extending inwardly from the wall of each recess (148), and a corresponding raised rib (146b) extending outwardly from tab (146). The detent system assists in preventing actuator (112) from rotation and fasteners (110) from moving out of fully retracted or fully extended fired states under vibration or incidental loads, as described below.

Actuator (112) includes a plurality of spaced apart openings or slots (154), which may be engaged by any suitable instrument to transmit the necessary torque to actuator (112) to extend fasteners (110) to the actuated position. Slots (154) are configured to be engaged by commercially available instruments, rectangular in the embodiment depicted, or by a dedicated applier described below. A merely exemplary applier that may be used to engage slots (154) to rotate actuator (112) for deployment of fasteners (110) is disclosed in U.S. Pub. No. 2005/0283118, entitled "Implantable Medical Device with Simultaneous Attachment Mechanism and Method," published Dec. 22, 2005, the disclosure of which is incorporated by reference herein. Port body (106) includes a plurality of recesses (156) disposed about its lower periphery which are configured to cooperate with the dedicated applier described in U.S. Pub. No. 2005/0283118. Various other structures, features, and operability that may be incorporated into injection port (100) are also described in U.S. Pub. No. 2005/0283118. It should also be understood that, while injection port (100) of the present example has integral fasteners (110), such features are merely optional. For instance, injection port (110) may instead be configured such that it is secured to a patient using separate tacks, sutures, staples, or using any other suitable devices, components, or techniques.

As noted above, the exemplary configuration of injection port (100) provides some degree of axial play of actuator (112) relative to port body (108) and septum retainer (104). That is, in addition to being rotatable (relative to port body (108) and septum retainer (104), etc.) about an axis of port (100) to selectively extend or retract fasteners (110), actuator (112) may slightly move up and down along that axis. As shown in FIGS. 7-8, a haptic feedback interface ring (202) is positioned between actuator (112) and port body (108). Haptic feedback interface ring (202) is operable to sense when actuator (112) is being pushed downwardly toward port body (108). Furthermore, and as will be described in greater detail below, port (100) may provide a vibratory response when interface ring (202) senses that actuator (112) is being pushed downwardly toward port body (108). This vibratory response may assist a physician in locating port (100) through external palpation after port (100) has been implanted in a patient. Interface ring (202) may comprise or form a switch that is in communication with a processor (204) (e.g., via wire, etc.) as will be described in greater detail below. Actuation of interface ring (202) by pushing downward on actuator (112) (e.g., by a physician palpating a patient, etc.) may thus actuate the corresponding switch, which may cause processor (204) to trigger the vibratory response.

In some versions, port (100) comprises one or more resilient members (not shown) that are configured to bias actuator (112) to an upper position. By way of example only, interface ring (202) may itself be configured to bias actuator (112) to an upper position. For instance, interface ring (202) may be resilient and may have a "wavy" configuration. Other ways in which actuator (112) may be biased to an upper position (regardless of whether actuator (112) is also rotatable) will be apparent to those of ordinary skill in the art in view of the teachings herein. Similarly, other suitable variations, components, features, and configurations of interface ring (202) will be apparent to those of ordinary skill in the art in view of the teachings herein. By way of example only, interface ring (202) may be substituted with one or more switches positioned between actuator (112) and port body (108), without a ring-shaped member being used to form a vibratory response activation interface between actuator (112) and port body (108). Such discrete switches may be equidistantly positioned about a circumference or be positioned in any other suitable locations/arrangement. As another merely illustrative example, port (100) may be configured such that interface ring (202) does not move up and down relative to port body (108). In some such versions, one or more strain gauges or other types of sensors may be used to determine whether a downward force is being exerted on actuator (112), with such sensors being configured to trigger a vibratory response as described in greater detail below. Alternatively, interface ring (202) may be omitted in some versions, including but not limited to those versions described in greater detail below.

In addition to providing some degree of axial play of actuator (112), port (100) may provide some degree of axial play for plate (128). In other words, plate (128) may slightly move up or down along the same axis about which actuator (112) rotates. Such axial play may be provided without sacrificing a hermetic seal between plate (128) and septum retainer (104) or between plate (128) and port body (108). As shown in FIGS. 7-8, a haptic feedback interface sensor (206) is positioned beneath plate (128). Interface sensor (206) is operable to sense when plate (128) is being pushed downwardly. Furthermore, and as will be described in greater detail below, port (100) may provide a vibratory response when interface sensor (206) senses that plate (128) is being pushed downwardly. This vibratory response may assist a physician in determining that a needle has struck plate (128), which may further indicate that the needle has been successfully inserted through septum (106). Interface sensor (206) may comprise or form a switch that is in communication with processor (204) (e.g., via wire, etc.) as will be described in greater detail below. Actuation of interface sensor (206) by pushing downward on plate (128) (e.g., by a needle striking plate (128), etc.) may thus actuate the corresponding switch, which may cause processor (204) to trigger the vibratory response.

In some versions, port (100) comprises one or more resilient members (not shown) that are configured to bias plate (128) to an upper position. By way of example only, interface sensor (206) may itself be configured to bias actuator (112) to an upper position. For instance, interface sensor (206) may comprise a resilient ring positioned between the outer perimeter of the underside of plate (128) and septum retainer (104), and such a ring may have a "wavy" configuration. Other ways in which plate (128) may be biased to an upper position will be apparent to those of ordinary skill in the art in view of the teachings herein. Similarly, other suitable variations, components, features, and configurations of interface sensor (206) will be apparent to those of ordinary skill in the art in view of the teachings herein.

In some other versions, port (100) may be configured such that plate (128) does not move up and down relative to septum retainer (104) and/or port body (108). It should be understood that, in some such versions, various types of interface sensors (206) may still be used to determine whether a downward force is being exerted on plate (128), with such sensors being configured to trigger a vibratory response as described in greater detail below. For instance, interface sensor (206) may comprise a thin film capacitive switch or strain gauge on plate (128). As yet another merely illustrative example, interface sensor (206) may simply detect the presence of a needle in fluid chamber (130), without necessarily detecting contact between the needle and plate (128) as such. For instance, interface sensor (206) may comprise a proximity sensor, an ultrawideband radar device, a metal detector that essentially ignores the metal of plate (128) while detecting the metal of a needle in fluid chamber (130), etc. Furthermore, it should be understood that interface sensor (206) need not necessarily be located under plate (128) (e.g., interface sensor (206) may be in fluid chamber (130), etc.). Still other suitable components and configurations that may be used for interface sensor (206) will be apparent to those of ordinary skill in the art in view of the teachings herein. Alternatively, interface sensor (206) may be omitted in some versions, including but not limited to those versions described in greater detail below.

In the present example, and as best seen in FIG. 8, injection port (100) also includes a chamber (200) located below plate (128). Chamber (200) is enclosed and hermetically sealed, such that chamber (200) is fluidly isolated relative to fluid chamber (130). Chamber (200) encloses several electrical components that are configured to provide vibratory responses as noted above. In particular, and as also shown in FIGS. 5 and 7-8, chamber (200) encloses processor (204), interface sensor (206), a power source (208), a vibration generator (210), and a storage device (212) (e.g., flash memory, memory chip, etc.). Of course, any or all of these components may be located elsewhere if desired. While these components are only shown in block form in the drawings, the various structural forms that these components may take will be apparent to those of ordinary skill in the art in view of the teachings herein. As best seen in FIG. 5, interface ring (202), interface sensor (206), power source (208), vibration generator (210), and storage device (212) are all in communication with processor (204) (e.g., via wires and/or traces in a circuit board, etc.). Processor (204) may comprise an off the shelf microprocessor, a customized processor (204), or any other suitable type of device or component. Processor (204) is configured to receive input from interface ring (202) and interface sensor (206), and is configured to trigger vibratory responses through vibration generator (210) as will be described in greater detail below. Processor (204) is also configured to interrogate storage device (212), and may also be configured to cause data to be stored on storage device (212).

Power source (208) of the present example comprises a conventional battery. It should be understood, however, that power source (208) may instead be substituted with a transcutaneous energy transfer (TET) coil, such that components shown in FIG. 5 are powered remotely by a coil that is external to the patient. For instance, in versions where port (100) includes a telemetry transceiver coil (214) as described in greater detail below, such a transceiver coil (214) may serve a dual role of receiving TET power and providing telemetric communication of data. As another merely illustrative example, where power source (208) comprises a battery, such a battery may be recharged through TET power. Still other suitable ways in which power may be provided to electrical/electronic components of port (100) will be apparent to those of ordinary skill in the art in view of the teachings herein.

In some versions, interface ring (202) and/or interface sensor (206) are omitted. In some such versions, vibration generator (210) is activated by an external coil. For instance, such an external coil may be configured in accordance with the teachings of U.S. Pub. No. 2006/0211914, entitled "System and Method for Determining Implanted Device Positioning and Obtaining Pressure Data," published Sep. 21, 2006, the disclosure of which is incorporated by reference herein. As another merely illustrative example, such an external coil may be configured in accordance with the teachings of U.S. Pat. No. 7,599,744, entitled "Transcutaneous Energy Transfer Primary Coil with High Aspect Ferrite Core," issued Oct. 6, 2009, the disclosure of which is incorporated by reference herein. Other suitable forms that such an external coil may take will be apparent to those of ordinary skill in the art in view of the teachings herein. In some versions where vibration generator (210) is activated by an external coil, telemetry transceiver coil (214) may be communicatively and transcutaneously coupled with the external coil. In particular, transceiver coil (214) and processor (204) may respond to a field generated by the external coil by activating vibration generator (210). In addition, the external coil and telemetry transceiver coil (214) may together provide power to vibration generator (210) via TET. Thus, a battery or other implanted power source (208) need not be included within port (100). It should be understood from the foregoing that a physician may locate port (100) by sweeping over the patient's abdomen and/or chest with the external coil until vibrations are felt from vibration generator (210). Such vibrations may reach a maximum intensity when the external coil is directly over port (100). The physician may then insert the needle through the center of external coil to reach port (100); or may first remove external coil then insert the needle where the center of the external coil was when vibrations from vibration generator (210) were at their maximum intensity.

In some versions where an external coil is used to activate vibration generator (210), vibration generator (210) comprises a conventional type of vibration generator (e.g., such as those described in greater detail below, etc.). In some such versions, the external coil simply activates vibration generator (210), which is actually powered by power source (208) within port (100). In other words, the field generated by the external coil simply acts as a switch to cause vibration generator (210) to generate vibrations. In some other versions where vibration generator (210) comprises a conventional type of vibration generator, the external coil provides power to vibration generator (210) through TET as described above. Of course, vibration generators (210) that are turned on by an external coil and/or are powered by an external coil need not be conventional, and may take any suitable form.

As yet another variation, an external coil may effectively form a vibration generator (210) with some component of port (100). For instance, port (100) may include some ferromagnetic or permanent magnet mass and/or some type of high permittivity element (e.g., iron, nickel-alloy, 400 series stainless steel, etc.) that couples with a field generated by the external coil. Such an internal element may be contained within port (100) (e.g., within chamber (200)) or may be secured to the exterior of port (100). An outer coil may be held on the outside of the patient's body and moved around the patient's abdomen and/or chest. As the outer coil approaches a space over port (100), the outer coil may excite the implanted mass. In particular, an alternating current in the external coil may alternatingly attract and repel the responsive mass in port (100), which may cause port (100) to vibrate.

Such vibration of port (100) may in turn guide the physician to the location and orientation of port (100) (e.g., based on the intensity of the vibration, etc.). As the physician inserts the needle in the patient (e.g., through the center of the external coil that is exciting the implanted element), the physician may be able to feel the vibration intensity change as the needle approaches the vibrating source. Once the inserted needle contacts strike plate (128), the intensity of the vibration may increase significantly, which may in turn provide confirmation to the physician that they have successfully penetrated septum (106) into reservoir (130) with the needle. Maximum vibration may occur at a resonant frequency, which the external coil may find using standard phase lock electronics. It should be understood that the frequency and/or amplitude at which the external coil operates during such a port-finding process may differ significantly from the frequency and/or amplitude at which the external coil operates during other TET/telemetry processes involving port (100). Various ways in which such versions of vibration generator (210) may be provided will be apparent to those of ordinary skill in the art in view of the teachings herein.

In some versions, vibration generator (210) comprises a reciprocating or oscillating weight. In particular, the weight may be provided by a permanent magnet (not shown) that is suspended by a resilient member (e.g., one or more springs, one or more diaphragms, etc.). A ring or coil (not shown) is selectively energized (e.g., by power source (208) and processor (204), etc.) to cause the permanent magnet weight to reciprocate or oscillate, which in turn causes vibration. Merely illustrative components and configurations that such a reciprocating weight type of vibration generator (210) may incorporate are disclosed in U.S. Pat. No. 7,292,227, entitled "Electronic Device, Vibration Generator, Vibration-Type Reporting Method, and Report Control Method," issued Nov. 6, 2007, the disclosure of which is incorporated by reference herein. Additional exemplary components and configurations that vibration generator (210) may incorporate are disclosed in U.S. Pat. No. 6,982,696, entitled "Moving Magnet Actuator for Providing Haptic Feedback," issued Jan. 3, 2006, the disclosure of which is incorporated by reference herein; and U.S. Pat. No. 5,800,336, entitled "Advanced Designs of Floating Mass Transducers," issued Sep. 1, 1998, the disclosure of which is incorporated by reference herein.

In some other versions, vibration generator (210) comprises a rotatable weight. In particular, the weight (not shown) may be located eccentric to an axis of rotation, and a motor (not shown) may rotate the weight, such that rotation of the eccentric weight causes vibration of port (100). Merely illustrative components and configurations that such a rotating eccentric weight type of vibration generator (210) may incorporate are also disclosed in U.S. Pat. No. 7,292,227. As another merely illustrative example, a rotating eccentric weight type of vibration generator (210) may be configured in accordance with the teachings of U.S. Pat. No. 5,107,155, entitled "Vibrator Motor for Wireless Silent Alerting Device," issued Apr. 21, 1992, the disclosure of which is incorporated by reference herein. By way of example only, the motor may rotate the weight at speeds up to approximately 10,000 rpm or at any other suitable speed.

As yet another merely illustrative example, vibration generator (210) may be configured to act between the patient's body and the entire mass of port (100). For instance, vibration generator (210) may comprise a reciprocating actuator that extends downwardly from the bottom of port (100) and that engages the tissue of the patient underneath port (100). In some such versions, the port (100) itself forms the vibrating mass of the vibration generator (210), and the patient's body provides a virtually infinite mass (relative to the mass of port (100)). Fasteners (110) or whatever other components are used to secure port (100) to the patient's tissue (e.g., tacks, sutures, staples, etc.), together with the patient's tissue in which such fasteners (110) or other components are inserted, may effectively provide an elastic member allowing port (100) as a vibrating mass to vibrate relative to the underlying tissue as the downwardly extending reciprocating actuator reciprocates against the patient's underlying tissue. The reciprocating actuator may provide a surface area of engagement with the patient's tissue that is large enough to raise port (100) up from the underlying tissue as the reciprocating actuator reciprocates, even if only to a slight degree. Such engagement between the reciprocating actuator and the patient's tissue may thus provide effective vibration of port (100) that can be felt by an externally palpating physician; rather than simply providing the patient with a sensation that they are being repeatedly poked by the reciprocating actuator with no externally palpable effect. By way of example only, the reciprocating actuator may comprise a diaphragm that extends across the bottom surface of port (100) and that directly engages the underlying tissue of the patient.

As another merely illustrative example, vibration generator (210) may comprise a piezoelectric element. By way of example only, vibration generator (210) may be configured in accordance with the teachings of U.S. Pat. No. 5,277,694, entitled "Electromechanical Transducer for Implantable Hearing Aids," issued Jan. 11, 1994, the disclosure of which is incorporated by reference herein. As another example, vibration generator (210) may be configured in accordance with the teachings of U.S. Pat. No. 7,583,564, entitled "Piezoelectric Actuator and Electronic Equipment with Piezoelectric Actuator," issued Sep. 1, 2009, the disclosure of which is incorporated by reference herein. In some other versions, vibration generator (210) may comprise a piezoelectric element that is contained within a clamshell housing. When the piezoelectric element is excited (e.g., by a transcutaneously applied field, by a signal from a wire that is coupled with the piezoelectric element, etc.), the outward motion of the piezoelectric element pushes outwardly on each half of the surrounding clamshell housing. A vibratory mass may be coupled with one of the clamshell halves, while the other clamshell half may be "grounded" or secured directly to port (100). Thus, if the piezoelectric element pushes upwardly a distance "x" and downwardly a distance "x," the displacement of the vibratory mass relative to the "ground" of port (100) would be "2x."

As yet another merely illustrative example, vibration generator (210) may comprise a magnetostrictive material. For instance, a magnetostrictive material may be provided as a coil that is wrapped around an inner shaft. The inner shaft may contain the exciting element that acts on the magnetostrictive material. For instance, the inner shaft may be formed by an electromagnet that is selectively activated at a frequency selected to provide a rapid expansion and contraction of the magnetorestrictive material. In particular, when the magnetostrictive material is selectively excited by the inner shaft, the magnetorestrictive material expands and contracts at a rapid rate, producing vibration as it hits upper and lower bounding diaphragms.

As another merely illustrative example, vibration generator (210) may comprise a lever arm that has a mass at one end and a piezoelectric element under the other end. The piezoelectric element and the fulcrum support of the lever arm may be "grounded" or secured directly to port (100). Other forms of vibration generator (210) may include one or more solenoids, rotational motors, steppers, etc. In some versions, a vibratory actuator within a vibration generator (210) acts a corporeal vibration/motion energy harvester. For instance, such an energy harvesting actuator may act as an actuator "run in reverse" while it is not actively vibrating port (100), to passively collect energy that can be stored in a battery or capacitor within port (100) for later use when vibration generator (210) needs to be activated to vibrate. Various ways in which a vibratory actuator (or other component) within vibration generator (210) or elsewhere can be configured to act as such an energy harvester will be apparent to those of ordinary skill in the art in view of the teachings herein. It should therefore be understood that vibration generator (210) may be powered by an implanted power source (208), by an external coil, and/or by an implanted energy harvester, including combinations thereof. Similarly, and regardless of whether an energy harvester is included, other suitable variations, components, features, and configurations of vibration generator (210) will be apparent to those of ordinary skill in the art in view of the teachings herein.

It should be understood that the choice of the mass of port (100) and the choice of the mass of a moving member in vibration generator (210) may determine a resonant frequency of vibration generator (210). For instance, such masses and resultant resonant frequencies may be selected in accordance with the teachings of Dietz, et al.; "Partially Implantable Vibrating Ossicular Prosthesis"; *Transducers '97*; International Conference on Solid State Sensors and Actuators; Chicago, Jun. 16-19, 1997; Vol. 1., pp. 433-436, the disclosure of which is incorporated by reference herein. Suitable resonant frequencies for vibration generator (210), as well as methods/equations for determining a resonant frequency of a vibration generator (210), will thus be apparent to those of ordinary skill in the art. In addition, it should be understood that vibration generator (210) may generate vibrations having any suitable amplitude and frequency. By way of example only, the vibration generated by vibration generator (210) may have an amplitude of approximately 100 micrometers within a frequency range of approximately 1 Hz and approximately 100 Hz. As another merely illustrative example, the vibration generated by vibration generator (210) may have an amplitude between approximately 100 micrometers and approximately 10 micrometers within a frequency range of approximately 5 Hz and approximately 100 Hz. As yet another merely illustrative example, the vibration generated by vibration generator (210) may have an amplitude between approximately 1000 micrometers and approximately 1 micrometer within a frequency range of approximately 10 Hz and approximately 800 Hz. Still other various suitable vibratory frequencies and amplitudes that may be generated by vibration generator (210) will be apparent to those of ordinary skill in the art in view of the teachings herein.

It should also be understood that vibration generator (210) may be used for a variety of purposes. One merely exemplary use for vibration generator (210) may be to assist a physician in locating port (100) after port (100) has been implanted in a patient. For instance, depending on the location of port (12) within the patient and the obesity of the patient, some physicians may have difficulty in locating a conventional implanted port (12). The physician may wish to locate port (12) in order to insert a needle into septum (16) to add fluid to or withdraw fluid from gastric band system (10). In some settings where port (12) includes a TET/telemetry coil, the physician may wish to locate port (12) in order to properly position an external coil or other type of antenna in order to provide power to and/or receive data from components in the port (12). Accordingly, where port (100) has been implanted in the patient, the physician may palpate the patient's abdomen and/or chest in order to locate port (100). When the physician palpates over the location of port (100), such palpation may press actuator (112) downward, which may activate interface ring (202), which may in turn activate vibration generator (210) to provide haptic feedback to the physician indicating that the port (100) is generally beneath the physician's hand. The physician may then insert the needle in this area to pierce septum (106) in order to add fluid to or withdraw fluid from gastric band system (10). In addition or in the alternative, and to the extent that port (100) includes a TET/telemetry coil (214), the physician may place an external coil or other type of antenna in this area in order to provide power to and/or receive data from coil (214) in port (100). In some versions where interface ring (202) or some functional equivalent thereof is omitted, vibration generator (210) may be activated by the presence of an RF field generated by a coil that is external to the patient, as noted above. It should therefore be understood that actuator (112) need not always be axially movable along the central axis defined by port (100).

In some settings, actuator (112) may occasionally be pressed down by the patient's own movements or positioning. It may be desirable to prevent such incidental pressing of actuator (112) from triggering a vibratory response by vibration generator (210). To that end, processor (204) may be configured to compare downward forces exerted on actuator (112) against a predetermined force threshold level, such that processor (204) only triggers vibration by vibration generator (210) when the downward force on actuator (112) exceeds the predetermined threshold. The force threshold may be selected such that incidental pressing on actuator (112) by patient movement/positioning falls below the threshold; while sufficient external palpation by a physician exceeds the threshold. Data representing such a force threshold may be stored on storage device (212). In some other variations, processor (204) may be configured such that it will not trigger vibration by vibration generator (210) unless the presence of some external signal is detected. For instance, control logic in processor (204) may be configured to cause processor (204) to ignore activations of interface ring (202) unless coil (214) is receiving some type of signal from a coil that is external to the patient. Such an external signal may thus simply "unlock" vibration generator (210), such that external palpation by a physician may activate vibration generator (210) only when vibration generator (210) is "unlocked" by the external signal. Alternatively, an external signal may directly cause vibration generator (210) to generate vibrations as noted above. Still other suitable ways in which port (100) may prevent a vibratory response to inadvertent pressing of actuator (112) will be apparent to those of ordinary skill in the art in view of the teachings herein. Of course, some versions of port (100) may lack such prevention; and some other versions of port (100) may lack a feature permitting actuator (112) to be pressed in relative to other portions of port (100).

Another merely exemplary use for vibration generator (210) may be to assist a physician in confirming that the needle has successfully reached fluid chamber (130) to adjust the amount/pressure of fluid in an implanted gastric band system (10). For instance, even when a physician has determined the general location of port (100) implanted in a patient, the physician may have difficulty determining whether a needle inserted in the patient has successfully reached fluid chamber (130). A physician may generally determine through tactile feedback felt through the needle and syringe that the needle has struck some hard object, but the physician may not be able to determine whether the needle has struck plate (128) or some other hard component of port (100) (e.g., needle may have instead struck actuator (112), port housing (108), etc.). Accordingly, when the physician has successfully inserted the needle into fluid chamber (130) and the needle has struck plate (128), such striking of plate (128) by the needle may activate interface sensor (206), which may in turn activate vibration generator (210) to provide haptic feedback to the physician indicating that the needle has reached fluid chamber (130). The physician may then use the syringe and needle to add fluid to or withdraw fluid from the implanted gastric band system (10), to adjust the size of the stoma created by gastric band (20).

In situations where the physician feels the inserted needle striking something hard but does not receive the vibratory response from vibration generator (210), such a lack of vibratory response may indicate to the physician that the needle has missed septum (106) (e.g., needle instead struck actuator (112), port housing (108), etc.) and that the needle is therefore not in fluid chamber (130). The physician may then partially or fully withdraw the needle and reposition it for another attempt to pierce septum (106) and reach fluid chamber (130). This process may be repeated until the physician finally receives haptic feedback from vibration generator (210) to indicate that the needle has successfully reached fluid chamber (130).

In some versions where port (100) includes both interface ring (202) and interface sensor (206), it may be desirable to vary the response from vibration generator (210) based on whether interface ring (202) or interface sensor (206) has been activated. This may be desirable in some settings to account for the possibility that a physician may strike actuator (112) with an inserted needle instead of striking plate (128). Making the vibratory response when interface sensor (206) is triggered different from the vibratory response when interface ring (202) is triggered may thus allow the physician to confirm that the inserted needle has struck plate (128) instead of actuator (112). The vibratory response from vibration generator (210) may differ in a variety of ways, including but not limited to frequency, waveform, magnitude, duration, and/or pulse pattern, etc., based on whether interface ring (202) or interface sensor (206) has been activated. Of course, some versions may provide the same vibratory response from vibration generator (210) regardless of whether interface ring (202) or interface sensor (206) has been activated. Furthermore, some versions of port (100) may have only interface ring (202) or only interface sensor (206); while lacking the other.

In some alternative versions, port (100) lacks interface sensor (206). In some such versions, vibration generator (210) is operable to generate externally palpable vibrations based on actuation of interface ring (202), based on the presence of an externally applied field, or based on some other form of activation. Furthermore, such vibrations may be sustained as a physician inserts a needle into a patient. Alternatively, such vibrations may be initiated upon the needle contacting an external portion of port (100). In some such versions, vibration generator (210) may cause the entire port (100) to vibrate. It should be understood that such vibrations may be acoustically coupled with the needle in different ways depending on the material of the port (100) that is struck by the needle. For instance, port body (108) (including annular rim (120)) and actuator (112) may be formed of a substantially hard material (e.g., plastic and/or metal, etc.); while septum (106) may be formed of a relatively soft material (e.g., silicone, etc.). Thus, when the needle strikes a relatively hard portion of vibrating port (100), the acoustic coupling may provide a "scratchy" vibratory sensation through the needle to the physician's hand. Such a tactile sensation may inform the physician that the needle is in contact with port (100) but not inserted through septum (106). The physician may then reposition the needle until the physician feels a "softer" vibratory sensation through the needle that would be associated with the needle being inserted through septum (106) of vibrating port (100). As one merely illustrative variation of this example, port (100) may be configured such that vibration is maximized at annular rim (120) surrounding septum (106), which may provide greater guidance to the physician who is attempting to locate (106) septum based on haptic/tactile feedback. For instance, portions of port (100) that are external to annular rim (120) may be vibrationally isolated or dampened relative to annular rim (120), such that those external portions either do not vibrate while annular rim (120) vibrate or such that the vibrations of those external portions have a lower amplitude than the vibrations of annular rim (120).

Yet another merely exemplary use for vibration generator (210) may be to provide an alert when some condition has been detected. By way of example only, some versions of port (100) may include a pressure sensor (216) that is configured to sense the pressure of fluid in gastric band system (10). Various suitable ways in which a pressure sensor (216) may be incorporated into gastric band system (10) are disclosed in U.S. Pub. No. 2006/0211914, entitled "System and Method for Determining Implanted Device Positioning and Obtaining Pressure Data," published Sep. 21, 2006, the disclosure of which is incorporated by reference herein. Alternatively, any other suitable type of pressure sensor (216) may be incorporated into gastric band system (10) in any suitable fashion. While FIG. 5 depicts pressure sensor (216) as a component of port (100), it should be understood that pressure sensor (216) may be located in any other suitable position or component.

Processor (204) may be configured to monitor readings from pressure sensor (216) and compare those readings to one or more baselines stored on storage device (212). Processor (204) may further be configured to trigger a vibratory response by vibration generator (210) when a pressure data reading from pressure sensor (216) deviates from a baseline or range. For instance, processor (204) may trigger a vibratory response by vibration generator (210) when the pressure of fluid in gastric band system (10) falls below a threshold (e.g., approximately 10 mmHg, etc.), which may indicate that there is a leak in the system (10), that more fluid needs to be added to system (10), or some other condition. Similarly, processor (204) may trigger a vibratory response by vibration generator (210) when the pressure of fluid in gastric band system (10) exceeds a threshold (e.g., approximately 50 mmHg, etc.), which may indicate that fluid needs to be withdrawn from system (10), or some other condition. Such pressure-based feedback may be felt by the patient, and may prompt the patient to contact their physician for an adjustment of gastric band (20). The physician may then investigate further and provide any appropriate medical response (e.g., adding fluid to or withdrawing fluid from gastric band system (10), etc.). By way of example only, pressure-based feedback that is provided to the patient may comprise a few short bursts of vibration provided every half hour, a slight vibration two or three times a day, etc. In some versions, only one threshold value is provided (e.g., either an upper threshold to trigger vibratory alert when exceeded or a lower threshold to trigger vibratory alert when fallen below).

Providing vibratory alerts to the patient to indicate the need for an adjustment of gastric band (20) upon detection of inappropriate fluid pressure levels may provide a more efficient program for weight loss in some settings. For instance, in the absence of such alerts, the patient may only visit their physician for adjustment of gastric band (20) based on how the gastric band (20) "feels" to the patient; and/or based on a predetermined schedule that may ultimately have the patient coming in for adjustments either too soon or too late. In some settings, the patient's weight loss might undesirably plateau if they do not visit their physician for an adjustment of gastric band (20) soon after the fluid pressure level has dropped below a certain level. Accordingly, in some situations, vibratory alerts to the patient to indicate the need for an adjustment of gastric band (20) may avoid such plateaus and may provide a substantially more linear progression of weight loss. Of course, such weight loss results might not occur in some settings, as some patients may still encounter weight loss plateaus or even not lose weight despite receiving vibratory alerts that indicate the need for an adjustment of gastric band (20). Furthermore, weight loss plateaus may even be desirable in some settings.

It should be understood that the vibratory response from vibration generator (210) may vary based on the conditions of the fluid pressure sensed by pressure sensor (216). For instance, processor (204) may initiate a vibratory response when the fluid pressure drastically and suddenly changes (e.g., indicating an emergency condition that needs to be immediately addressed, etc.) that is different from the vibratory response initiated by processor (204) when the fluid pressure gradually changes (e.g., indicating a non-emergency condition, etc.). The vibratory response from vibration generator (210) may differ in a variety of ways, including but not limited to frequency, waveform, magnitude, duration, and/or pulse pattern, etc., based on fluid pressure conditions sensed by pressure sensor (216). It should also be understood that a variety of other types of sensors may be coupled with processor (204), and that parameters detected by such sensors may also be used to trigger a response from vibration generator (210).

Still another merely exemplary use for vibration generator (210) may be to simply remind the patient to observe a proper diet. That is, the patient may have received a gastric band system (10) due to the patient's morbid obesity, and part of the patient's treatment plan may include a proper/prescribed diet in addition to the implantation of a gastric band system (10). Processor (204) may be configured to send brief vibration bursts through vibration generator (210) around mealtime to remind the patient of their prescribed diet. Of course, as with other features described herein, this feature is merely optional.

As noted above, port (100) may be secured within patient by swiveling fasteners (110), with fasteners (110) being swiveled to the extended/deployed position upon rotation of actuator (112). As also noted above, ribs (148a, 148b) and ribs (146b) of port (100) provide a detent system that provides resistance to inadvertent rotation of actuator (112), thereby providing resistance to inadvertent retraction of swiveling fasteners (110). It should also be understood that this detent system may also provide resistance to inadvertent rotation of actuator (112) that might otherwise be caused by vibration of vibration generator (210). Of course, a variety of other structures, components, features, or configurations may be used to prevent or resist inadvertent rotation of actuator (112) that might otherwise be caused by vibration of vibration generator (210). Furthermore, port (100) might lack swiveling fasteners (110) and might be secured within the patient in some other fashion. By way of example only, port (100) may be secured within the patient using sutures, tacks, staples, biosurgical adhesive, and/or using any other suitable components, devices, or techniques, including combinations thereof.

In some settings, it may be desirable to deactivate vibration generator (210) until port (100) has been implanted in the patient. In other words, it may be desirable in some settings to prevent vibration generator (210) from vibrating before and during the process of installing port (100) in the patient. Otherwise, pressing of actuator (112) during the process of installing port (100) in the patient might activate interface ring (202) and thereby cause vibration generator (210) to vibrate. There are a variety of ways in which vibration generator (210) may be disabled before installation of port (100) is complete. For instance, one or more bosses or other types of mechanical lockout feature may prevent actuator (112) from being moved downwardly toward port body (108) until after actuator (112) has been rotated to deploy fasteners (110) to the extended position. As another merely illustrative example, actuator (112) and/or interface ring (202) may be configured such that downward movement of actuator (112) does not engage interface ring (202) until after actuator (112) has been rotated to deploy fasteners (110) to the extended position. As yet another merely illustrative example, port (110) may include a switch or other feature that enables interface ring (202), with such a switch or other feature being engaged by actuator (112) after actuator (112) has been rotated to deploy fasteners (110) to the extended position. Still other suitable ways in which rotation of actuator (112) to the fastener (110) deploying position may be required in order to enable vibration of vibration generator (210) will be apparent to those of ordinary skill in the art in view of the teachings herein.

As yet another variation, port (100) may be configured such that vibration generator (210) is unable to vibrate (even if actuator (112) is pressed downward) until after an initial enabling signal has been transmitted from an external coil to coil (214) of port (100). In other words, processor (204) may include a logic that requires coil (214) to first receive an unlocking signal or enablement signal before processor (204) will command vibration generator (210) to vibrate in response to actuator (112) being pressed downward. A physician may provide such an unlocking signal or enablement signal after port (100) has been installed in the patient. Vibration generator (210) may then be enabled to vibrate in response to downward pressing on actuator (112), even if such an external unlocking signal or enablement signal is no longer being transmitted to coil (214). In a relatively simpler version, port (100) may simply include a switch on its exterior that the physician may manipulate in order to make vibration generator (210) responsive to downward pressing on actuator (112). Still various other suitable ways in which responsiveness of vibration generator (210) may be selectively enabled and/or disabled will be apparent to those of ordinary skill in the art in view of the teachings herein.

While interface ring (202) and interface sensor (206) both "share" a common vibration generator (210) and processor (204) in the present example, it should be understood that interface ring (202) and interface sensor (206) may alternatively each have their own dedicated vibration generator (210) and/or processor (204). Accordingly, the inventors contemplate that the components shown in FIG. 5 may alternatively be provided in various other suitable numbers and/or arrangements. Furthermore, each of the components shown in FIG. 5 is merely optional.

Figure 9:
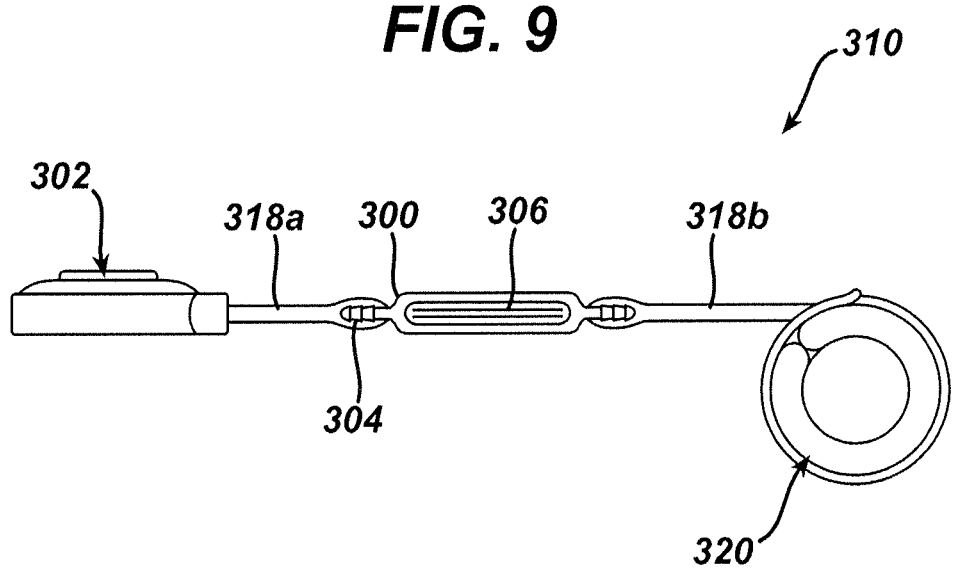
FIG. 9 depicts a schematic view of an exemplary alternative gastric band system.

It should also be understood that a vibration generator (210) may be used to facilitate palpatory location of various other implanted devices. For instance, FIG. 9 shows an alternative gastric band system (310) where a pressure sensing assembly (300) is placed in-line between injection port (302) and gastric band (320). Injection port (302) may comprise a conventional injection port (12), an injection port (100) like the one shown in FIGS. 5-8, or some other type of injection port. Gastric band (320) may comprise a conventional gastric band (20) or some other type of gastric band. A first catheter segment (318a) extends from injection port (302) and a second catheter segment (318b) extends from gastric band (320). Catheter segments (318a, 318b) are coupled with pressure sensing assembly (300) via barbed connectors (304). Of course, any other suitable type of connection may be provided in addition to or in lieu of barbed connectors (304). Pressure sensing assembly (300) comprises a pressure sensing module (306) that is in fluid communication with the fluid of this modified gastric band system (310). Pressure sensing module (306) of this example has certain components that are included in the previous example of injection port (100) and that are shown in FIG. 5. In particular, pressure sensing module (306) of this example comprises a processor (204), a power source (208), a vibration generator (210), a storage device (212), a telemetry coil (214), and a pressure sensor (216). As in some versions of port (100), power source (208) may be eliminated from pressure sensing module (306), particularly when telemetry coil (214) (or some other coil) is configured to receive TET power from an external source. In the present example, pressure sensor (216) is configured to sense the pressure of fluid in this gastric band system (310), while coil (214) is configured to transmit pressure data to an interrogating coil that is external to the patient.

Continuing with the example shown in FIG. 9, it may be desirable to facilitate location of an implanted pressure sensing assembly (300). While such location may not be necessary in order to make adjustments to the amount of fluid in gastric band system (310) in this example, such location may be necessary or otherwise desired in order for the physician to determine where to position an external coil or antenna to communicate with implanted coil (214) of pressure sensing assembly (300). Vibration generator (210) in pressure sensing assembly (300) may facilitate such location of pressure sensing assembly (300) by the physician. For instance, pressure sensing assembly (300) may include a feature that is analogous to interface ring (202) or interface sensor (206) as described above with respect to port (100). Such a ring (202) or sensor (206) may be coupled with a movable component of pressure sensing assembly (300) or some other part of pressure sensing assembly (300) that would permit the ring (202) or sensor (206) to respond to palpation of the patient in a region over pressure sensing assembly (300). Such a ring (202) or sensor (206) may also be in communication with processor (204) of pressure sensing assembly (300), with processor (204) being in communication with vibration generator (210). Accordingly, pressure sensing assembly (300) may be configured such that vibration generator (210) in pressure sensing assembly (300) provides a vibratory response as haptic feedback to a physician who palpates the patient above pressure sensing assembly (300). In other words, implanted pressure sensing assembly (300) may be located just like implanted port (100) described above. Upon determining the approximate location of pressure sensing assembly (300) through haptic feedback, the physician may accordingly position the external coil or antenna to interrogate and/or provide TET power to implanted coil (214).

While pressure sensing assembly is positioned in line between injection port (302) and gastric band (320) in the foregoing example, it should be understood that the teachings of this example could easily be incorporated into a gastric band system (310) where a pressure sensing assembly (300) is coupled with a "T" or "Y" connector that is joined to catheter segments (318a, 318b). For instance, a third catheter segment (not shown) may couple pressure sensing assembly (300) with the "T" or "Y" connector. As yet another merely exemplary variation, gastric band system (310) may be configured such that port (302) is between pressure sensing assembly (300) and gastric band (320) in the fluid circuit. Alternatively, any other suitable configuration or arrangement may be used.

As yet another example, gastric band system (10) may include an implanted pump/reservoir system (not shown) instead of including an injection port (12). Such a pump/reservoir system may be controlled to selectively vary the amount of fluid in gastric band (20). Examples of such a system are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Such systems may include an implanted coil such that they may be powered, controlled, and/or otherwise communicated with by an external coil or antenna. Accordingly, like pressure sensing assembly (300) described above, such systems may include various components shown in FIG. 5 to provide haptic feedback to a physician palpating the patient. That is, a physician may be trying to find the approximate location of the implanted coil to determine where to position the external coil, and the physician may palpate the patient until the physician locates the implanted coil through haptic feedback generated by a vibration generator (210) implanted with the pump/reservoir system. Upon discovering the approximate location of the pump/reservoir system through such haptic feedback, the physician may position the external coil accordingly and control the pump/reservoir system through signals emitted by the external coil.

It should be understood from the foregoing that vibration generators (210) may be incorporated into virtually any type of implanted device. The above described examples of gastric band systems are mere illustrations. The inventors' contemplation is not limited to components of gastric band systems. By way of example only, a vibration generator (210) may be incorporated into an implanted drug infusion port, chemotherapy port, or any other type of implantable port that is used to deliver medication, to help a physician locate the implanted port through palpation of the patient. Still other types of implanted devices that may incorporate a vibration generator (210) will be apparent to those of ordinary skill in the art in view of the teachings herein.

To the extent that a pressure sensor (216) is included in a gastric band system (10, 310), pressure data obtained using pressure sensor (216) may be processed and presented on a display device (not shown) in a variety of ways. In addition, the user may react to such pressure data in a variety of ways. Various suitable ways in which pressure data may be processed, presented, and reacted to are disclosed in U.S. Pub. No. 2008/0250340, entitled "GUI for an Implantable Restriction Device and Data Logger," published Oct. 9, 2008, the disclosure of which is incorporated by reference herein. Other ways in which pressure data may be processed, presented, and reacted to are disclosed in U.S. Pub. No. 2006/0211914, entitled "System and Method for Determining Implanted Device Positioning and Obtaining Pressure Data," published Sep. 21, 2006, the disclosure of which is incorporated by reference herein. Still other suitable ways in which pressure data may be processed, presented, and reacted to will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an implantable device;
   (b) a first sensor, wherein the first sensor is configured to detect a force exerted on a first portion of the implantable device through a patient's skin, wherein the first sensor is configured to be in communication with an exterior portion of the implantable device;
   (c) a second sensor, wherein the implantable device is configured to contain fluid, wherein the second sensor is configured to sense the pressure of fluid contained in the implantable device;
   (d) a vibration generator, wherein the vibration generator is co-located with the implantable device, wherein the vibration generator is in communication with the first sensor, wherein the vibration generator is configured to generate vibrations in response to the first sensor detecting a force exerted on the first portion of the implantable device through a patient's skin, wherein the vibration generator is further configured to generate vibrations in response to the first sensor detecting a force exerted on the exterior portion of the implantable device; and
   (e) a processor in communication with the second sensor, wherein the processor is configured to compare fluid pressure levels sensed by the second sensor against one or more threshold values, wherein the processor is further in communication with the vibration generator, wherein the processor is configured to cause the vibration generator to generate vibrations in response to the fluid pressure levels sensed by the second sensor either exceeding or falling below the one or more threshold values.

2. The apparatus of claim 1, wherein the implantable device comprises an injection port having a septum and a fluid chamber.

3. The apparatus of claim 2, wherein the injection port further comprises one or more integral fasteners, wherein the injection port comprises an actuator configured to move the one or more integral fasteners from a retracted position to an extended position.

4. The apparatus of claim 3, wherein the injection port further comprises a port body, wherein the actuator further comprises an actuator ring, wherein the actuator ring is rotatable relative to the port body about an axis, wherein the actuator ring is further operable to move longitudinally along the axis.

5. The apparatus of claim 4, wherein the first sensor is positioned between the actuator ring and the port body to detect downward movement of the actuator ring along the axis caused by palpation of the patient.

6. The apparatus of claim 2, wherein the first portion of the implantable device comprises a plate, wherein the septum defines a top portion of the fluid chamber, wherein the plate is spaced away from the septum and defines a bottom portion of the fluid chamber, wherein the plate is configured to restrict depth of insertion of a needle through the septum.

7. The apparatus of claim 6, wherein the first sensor is configured to sense a needle inserted through the patient's skin striking the plate.

8. The apparatus of claim 6, wherein the implantable device further defines a component chamber under the plate, wherein one or both of the first sensor or the vibration generator are located in the component chamber.

9. The apparatus of claim 1, wherein the second sensor is configured to detect a force exerted on a second portion of the implantable device through a patient's skin, wherein the vibration generator is further configured to generate vibrations in response to the second sensor detecting a force exerted on the second portion of the implantable device through a patient's skin.

10. The apparatus of claim 9, wherein the implantable device further comprises an interior portion, wherein the second portion of the implantable device is located in the interior portion of the implantable device.

11. The apparatus of claim 9, wherein the vibration generator is configured to provide a first type of vibratory response in response to the first sensor detecting a force exerted on the first portion of the implantable device through a patient's skin, wherein the vibration generator is configured to provide a second type of vibratory response in response to the second sensor detecting a force exerted on the second portion of the implantable device through a patient's skin.

12. An apparatus, comprising:
(a) an implantable device;
(b) a first sensor, wherein the first sensor is configured to detect a force exerted on a first portion of the implantable device through a patient's skin;
(c) a second sensor, wherein the implantable device is configured to contain fluid, wherein the second sensor is configured to sense the pressure of fluid contained in the implantable device;
(d) a vibration generator, wherein the vibration generator is co-located with the implantable device, wherein the vibration generator is in communication with the first sensor, wherein the vibration generator is configured to generate vibrations in response to the first sensor detecting a force exerted on the first portion of the implantable device through a patient's skin; and
(e) a processor in communication with the second sensor, wherein the processor is configured to compare fluid pressure levels sensed by the second sensor against one or more threshold values, wherein the processor is further in communication with the vibration generator, wherein the processor is configured to cause the vibration generator to generate vibrations in response to the fluid pressure levels sensed by the second sensor either exceeding or falling below the one or more threshold values.

13. The apparatus of claim 1, wherein the first sensor comprises a piezoelectric sensor.

* * * * *